United States Patent
Manzer

(10) Patent No.: US 7,067,677 B2
(45) Date of Patent: *Jun. 27, 2006

(54) PRODUCTION OF DIHYDRONEPETALACTONE BY HYDROGENATION OF NEPETALACTONE

(75) Inventor: Leo Ernest Manzer, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/405,444

(22) Filed: Apr. 2, 2003

(65) Prior Publication Data

US 2003/0225290 A1 Dec. 4, 2003

Related U.S. Application Data

(60) Provisional application No. 60/369,470, filed on Apr. 3, 2002.

(51) Int. Cl.
*C07D 311/42* (2006.01)

(52) U.S. Cl. ...................................... 549/283; 549/273
(58) Field of Classification Search ................. 549/283, 549/273
See application file for complete search history.

(56) References Cited

U.S. PATENT DOCUMENTS 3,978,000 A   8/1976   Schmitt, Jr. et al.

FOREIGN PATENT DOCUMENTS

DE          27 19 006         11/1977

OTHER PUBLICATIONS

Tsutomu Sakai, et al. "New Monoterpene Lactones of the Iridane Type from Actinidia polygama Miq", Bull Chem. Soc. Jpm, Dec. 1980, pp. 3683–2686, vol. 53, No. 12, Osaka.

F.E. Regnier, et al., Studies on the Composition of the Essential Oils of Three Nepeta Species, Pergamon Press Ltd., Phytochemistry, 1967, pp. 1281 to 1289, vol. 6, England.

Wolinsky, et al., "Synthesis of the Dihydronepetalactones", J. Org. Chem., (1972), pp. 3376–3378, Lafayette, Indiana.

Franco Bellesia, et al., "Synthesis and Molecular Structures of (1S)–cis, cis–Iridolactones", J.C.S.Perkin II, (197)(, pp. 1341–1346, Italy.

International Search Report dated Jul. 14, 2003.

U.S. Appl. No. 10/392,455.

H.L. Depooter et al., The Essential Oil of Five Nepeta Species. A Preliminary Evaluation of their use in Chemotaxonomy by Cluster Analysis, Flavour and Fragrance Journal, 1988, pp. 155–159, vol. 3.

N.V. Handjieva et al., Constituents of Essential Oils From Nepeta Cataria L. Grandiflora M.B. and N. Nuda L, J. Essential or Res., 1996, pp. 639–643, vol. 8.

H. Jin et al., The Shape–Selectivity of Activated Carbon Fibers as a Palladium Catalyst Support, Carbon, pp. 1996, 429–431, vol. 34.

T. Mallat et al., Phase Structure of Carbon Supported Palladium–Copper Catalysts, Applied Surface Science, 1990, pp. 309–313, vol. 40.

M. Gurrath et al., Palladium Catalysts on Activated Carbon Supports Influence of Reduction Temperature, Origin of the Support and Pretreatments of the Carbon Surface, Carbon, 2000, pp. 1241–1255, vol. 38.

P. Albers et al., Investigations of Palladium Catalyst on Different Carbon Supports, J. Catal., 1999, pp. 145–154, vol. 181.

Yu A. Ryndin et al., Supported Metallic Catalysts Obtained by Anchoring Metal Complexes on Carbon Supporst, J. Mol. Catal., 1989, pp . 109–125, vol. 55.

*Primary Examiner*—Bernard Dentz

(57) ABSTRACT

This invention relates to a process for hydrogenating nepetalactone, utilizing a metal catalyst that is optionally supported, to yield dihydronepetalactone. A suite of supported catalytic metals lead to rapid hydrogenation and high selectivity for dihydronepetalactone.

20 Claims, 1 Drawing Sheet

(4aS,7S,7aR) nepetalactone
(cis,trans-nepetalactone)

(4aR,7S,7aS) nepetalactone
(cis,cis-nepetalactone)

(4aS,7S,7aS) nepetalactone
(trans,cis-nepetalactone)

(4aR,7S,7aR) nepetalactone
(trans,trans-nepetalactone)

PRODUCTION OF DIHYDRONEPETALACTONE BY HYDROGENATION OF NEPETALACTONE

This application claims the benefit of U.S. Provisional Application No. 60/369,470, filed Apr. 3, 2002, which is incorporated in its entirety as a part hereof for all purposes.

FIELD OF THE INVENTION

This invention relates to a process for hydrogenating nepetalactone, utilizing a metal catalyst that is optionally supported, to yield dihydronepetalactone.

BACKGROUND OF THE INVENTION

Many plant species belonging to the family Labiatae (Lamiaceae) produce essential oils (aromatic oils) which are used as natural sources of insect repellent and fragrant chemicals [Hay, R. K. M. and Svoboda, K. P. *Botany, In "Volatile Oil Crops: their biology, chemistry and production"*; Hay, R. K. M., Waterman, P. G. (eds.); Longman Group UK Limited (1993)]. Plants of the genus Nepeta (catmints) are included as members of this family, and produce an essential oil which is a minor item of commerce. This oil is very rich in a class of monoterpenoid compounds known as iridoids [Inouye, H. *Iridoids. Methods in Plant Biochemistry* 7:99–143 (1991)], more specifically the methylcyclopentanoid nepetalactones [Clark, L. J. et al. *The Plant Journal*, 11:1387–1393 (1997)] and derivatives.

Four stereoisomers of nepetalactone are known to exist in nature, which may be readily obtained from different species within the plant genus Nepeta. These chemicals exert a well-known excitatory effect on cats [Tucker, A. O. and S. S. Tucker. *Economic Botany* 42: 214–231 (1988)], thus the oil—or more commonly, the dried herbage of this plant termed catnip—is used in cat toys. The leaves and oil of Nepeta spp. do not possess a particularly attractive aroma. The uses of the herbage and oil has therefore been confined to the small market offered by domestic cat toys and accessories. A small proportion of the oil of various Nepeta spp. consists of dihydronepetalactones, which are possibly derived biosynthetically from the more abundant nepetalactones [Regnier, F. E., et al. *Phytochemistry* 6:1281–1289 (1967); DePooter, H. L., et al. *Flavour and Fragrance Journal* 3:155–159 (1988); Handjieva, N. V. and S. S. Popov. *J. Essential Oil Res.* 8:639–643 (1996)].

Iridoid monoterpenoids have long been known to be effective repellents to a variety of insect species [Eisner, T. *Science* 146:1318–1320 (1964); Eisner, T. *Science* 148:966–968 (1965); Peterson, C. and J. Coats, *Pesticide Outlook* 12:154–158 (2001); and Peterson, C. et al. *Abstracts of Papers American Chemical Society*, (2001) 222 (1–2): AGRO73]. However, studies of the repellency of dihydronepetalactones have been much less conclusive [Cavill, G. W. K., and D. V. Clark. *J. Insect Physiol.* 13:131–135 (1967); Cavill, G. W. K., et al. *Tetrahedron* 38:1931–1938 (1982); Jefson, M., et al. *J. Chemical Ecology* 9:159–180 (1983)]. Recent studies have indicated that dihydronepetalactones may exert a repellent effect on the common insect pests of human society. Thus, a source of dihydronepetalactones (or a precursor) capable of supplying these compounds economically and in quantity may be required to allow commercial application of these molecules as insect repellents.

Additionally, it has been proposed that dihydronepetalactone compounds be used as fragrance materials. In view of these considerations, a source of dihydronepetalactones (or a precursor) capable of supplying these compounds economically and in quantity may also be required to allow commercial application of these molecules as fragrance materials.

Processes for hydrogenating iridoid monoterpene lactones (e.g., isoneonepetalactone, isodehydroiridomyrmecin, and isoactinidialactone) have been reported using platinum oxide ($PtO_2$) catalyst [Sakai, T. et al. *Bull. Chem. Soc. Jpn.*, 53(12): 3683–6 (1980)]. Likewise, neonepetalactone and isoneonepetalactone were hydrogenated with $PtO_2$ in $Et_2O$ and with Raney Ni in ethanol [Sakai, T. et al. Koen Yoshishu—Koryo, Terupen oyobi Seiyu Kagaku ni kansuru Toronkai, 23rd (1979), 45–48; Publisher: Chem. Soc. Japan, Tokyo, Japan].

Using similar methodology, processes for producing dihydronepetalactones by hydrogenation of nepetalactone are described in Regnier, R. E. et al. [*Phytochemistry* 6:1281–1289 (1967)]. Specifically, nepetalactone was treated with hydrogen and platinum oxide ($PtO_2$) catalyst to yield 53% methyl-2-isopropyl-5-methylcyclopentane-carboxylate, 2.8% α-dihydronepetalactone, and 35% δ-dihydronepetalactone.

When a palladium catalyst supported on strontium carbonate ($Pd/SrCO_3$) was used, 90% α-dihydronepetalactone, 3% methyl-2-isopropyl-5-methylcyclopentane-carboxylate, and a trace of δ-dihydronepetalactone was formed.

Both of these strategies for hydrogenation are limited, however; $PtO_2$ is an unsupported catalyst which permitted formation of a significant amount of open-ring derivatives, while $SrCO_3$ is an expensive support.

A need thus remains for an economical, efficient process for the production of dihydronepetalactones. The metals selected for use as catalysts in the process of this invention provide the desired economy and efficiency of production with a high degree of selectivity to the dihydronepetalactone product.

SUMMARY OF THE INVENTION

One embodiment of this invention is a process for the production of a dihydronepetalactone of formula (II) by hydrogenating a nepetalactone of formula (I) according to the following scheme:

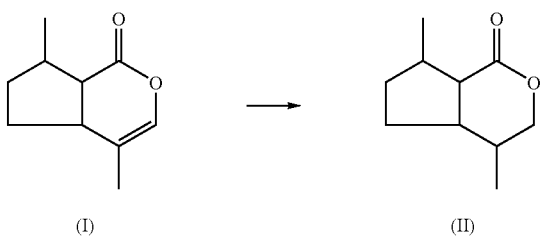

(I)          (II)

in the presence of a catalytic metal that is not nickel, platinum or palladium.

Another embodiment of this invention is a process for the production of a dihydronepetalactone of formula (II) by hydrogenating a nepetalactone of formula (I) according to the following scheme:

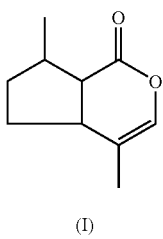  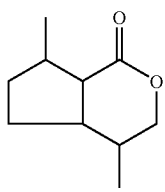

(I)　　　　　　　　(II)

in the presence of a catalytic metal selected from one or more members of the group consisting of nickel supported on a catalyst support, elemental platinum, platinum supported on a catalyst support, palladium not supported on a catalyst support, and palladium supported on a catalyst support that is not $SrCO_3$.

DETAILED DESCRIPTION OF THE INVENTION

The term "nepetalactone" as used herein refers to the compound having the general structure, as defined by Formula I:

Formula 1

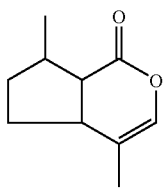

Figure 1:
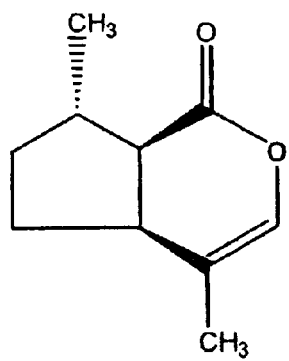
FIG. 1 shows the chemical structures of the naturally-occurring iridoid (methylcyclopentanoid) nepetalactones.
Figure 1:
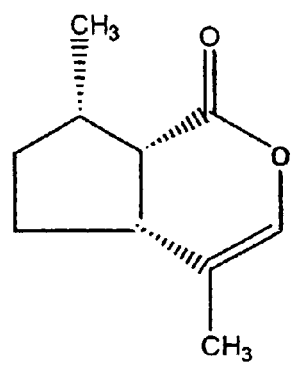
Figure 1:
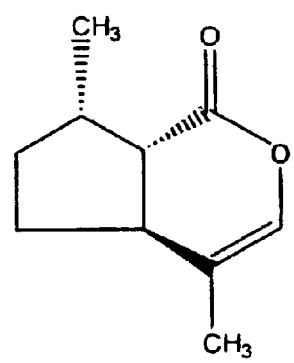
Figure 1:
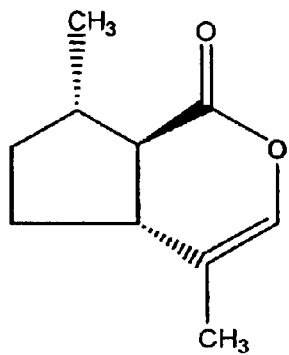

Four stereoisomers of nepetalactone are known to exist in nature, as shown in FIG. 1.

The term "dihydronepetalactones" or "dihydronepetalactone mixtures" as used herein refers to any mixture of dihydronepetalactone stereoisomers. The molar or mass composition of each of these isomers relative to the whole dihydronepetalactone composition can be variable. Dihydronepetalactones are defined by Formula 2:

Formula 2

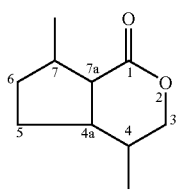

wherein 4, 4a, 7 and 7a indicate the four chiral centers of the molecule and the structure encompasses all possible stereoisomers of dihydronepetalactone.

The structures of dihydronepetalactone stereoisomers that may be derived from (7S)-nepetalactones are shown below.

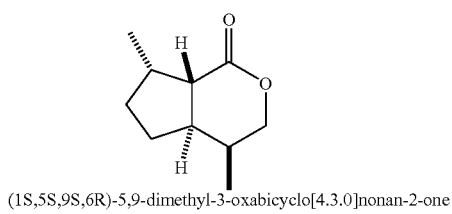

(1S,5S,9S,6R)-5,9-dimethyl-3-oxabicyclo[4.3.0]nonan-2-one

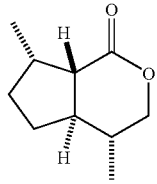

(1S,9S,5R,6R)-5,9-dimethyl-3-oxabicyclo[4.3.0]nonan-2-one

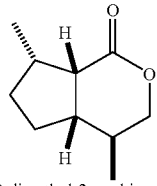

(1S,5S,9S,6S)-5,9-dimethyl-3-oxabicyclo[4.3.0]nonan-2-one

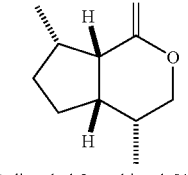

(1S,9S,6S,5R)-5,9-dimethyl-3-oxabicyclo[4.3.0]nonan-2-one

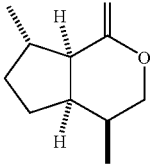

(9S,5S,1R,6R)-5,9-dimethyl-3-oxabicyclo[4.3.0]nonan-2-one

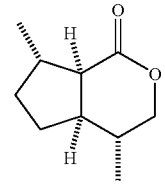

(9S,1R,5R,6R)-5,9-dimethyl-3-oxabicyclo[4.3.0]nonan-2-one

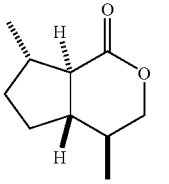

(9S,6S,1R,5S)-5,9-dimethyl-3-oxabicyclo[4.3.0]nonan-2-one

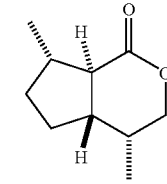

(9S,6S,1R,5R)-5,9-dimethyl-3-oxabicyclo[4.3.0]nonan-2-one

The term "catalyst" as used herein refers to a substance that affects the rate of a chemical reaction (but not the reaction equilibrium) and emerges from the process chemically unchanged.

The term "promoter" as used herein is a compound that is added to enhance the physical or chemical function of a catalyst. A chemical promoter generally augments the activity of a catalyst and may be incorporated into the catalyst during any step in the chemical processing of the catalyst constituent. The chemical promoter generally enhances the physical or chemical function of the catalyst agent, but can also be added to retard undesirable side reactions. A "metal promoter" refers to a metallic compound that is added to enhance the physical or chemical function of a catalyst.

Nepetalactones

Nepetalactone is a known material that can be conveniently obtained in relatively pure form from the essential oils isolated by various means from plants of the genus Nepeta (catmints). Isolation of such oils is well known in the art, and examples of methodology for oil extraction include (but are not limited to) steam distillation, organic solvent extraction, microwave-assisted organic solvent extraction, supercritical fluid extraction, mechanical extraction and enfleurage (initial cold extraction into fats followed by organic solvent extraction).

The essential oils isolated from different Nepeta species are well known to possess different proportions of each naturally-occurring stereoisomer of nepetalactone [Regnier, F. E., et al. *Phytochemistry* 6:1281–1289 (1967); DePooter, H. L., et al. *Flavour and Fragrance Journal* 3:155–159 (1988); Handjieva, N. V. and S. S. Popov. *J. Essential Oil Res.* 8:639–643 (1996)]. Thus, from oil derived from any Nepeta species containing a mixture of nepetalactones, a mixture of dihydronepetalactone stereoisomers will be generated upon hydrogenation. Four chiral centers are present within the methylcyclopentanoid backbone of the nepetalactone at carbons 4, 4a, 7 and 7a as shown below:

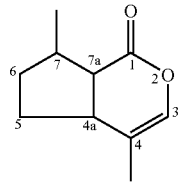

Thus it is clear that a total of eight pairs of dihydronepetalactone enantiomers are possible after hydrogenation of these, the naturally occurring stereoisomers described thus far are (7S)-dihydronepetalactones.

Hydrogenation

Hydrogenation of nepetalactone is effected in the presence of a suitable active metal hydrogenation catalyst. Acceptable solvents, catalysts, apparatus, and procedures for hydrogenation in general can be found in Augustine, *Heterogeneous Catalysis for the Synthetic Chemist*, Marcel Decker, New York, N.Y. (1996).

Many hydrogenation catalysts are effective, including (without limitation) those containing as the principal component iridium, palladium, rhodium, nickel, ruthenium, platinum, rhenium, compounds thereof, combinations thereof, and the supported versions thereof.

The metal catalyst used in the process of this invention may be used as a supported or as an unsupported catalyst. A supported catalyst is one in which the active catalyst agent is deposited on a support material by spraying, soaking or physical mixing, followed by drying, calcination, and if necessary, activation through methods such as reduction or oxidation. Materials frequently used as support are porous solids with high total surface areas (external and internal) which can provide high concentrations of active sites per unit weight of catalyst. The catalyst support may enhance the function of the catalyst agent; and supported catalysts are generally preferred because the active metal catalyst is used more efficiently. A catalyst which is not supported on a catalyst support material is an unsupported catalyst.

The catalyst support can be any solid, inert substance including, but not limited to, oxides such as silica, alumina, titania, calcium carbonate, barium sulfate, and carbons. The catalyst support can be in the form of powder, granules, pellets, or the like. A preferred support material of the present invention is selected from the group consisting of carbon, alumina, silica, silica-alumina, titania, titania-alumina, titania-silica, barium, calcium, compounds thereof and combinations thereof. Suitable supports include carbon, $SiO_2$, $CaCO_3$, $BaSO_4$ and $Al_2O_3$. Moreover, supported catalytic metals may have the same supporting material or different supporting materials.

In one embodiment of the instant invention, a more preferred support is carbon. Further preferred supports are those, particularly carbon, that have a surface area greater than 100–200 $m^2/g$. Further preferred supports are those, particularly carbon, that have a surface area of at least 300 $m^2/g$.

Commercially available carbons which may be used in this invention include those sold under the following trademarks: Bameby & Sutcliffe™, Darco™, Nuchar™, Columbia JXN™, Columbia LCK™, Calgon PCB™, Calgon BPL™, Westvaco™, Norit™ and Barnaby Cheny NB™. The carbon can also be commercially available carbon such as Calsicat C, Sibunit C, or Calgon C (commercially available under the registered trademark Centaur®).

Preferred combinations of catalytic metal and support system include
nickel on carbon,
nickel on $Al_2O_3$,
nickel on $CaCO_3$,
nickel on $BaSO_4$,
nickel on $SiO_2$,
platinum on carbon,
platinum on $Al_2O_3$,
platinum on $CaCO_3$,
platinum on $BaSO_4$,
platinum on $SiO_2$,
palladium on carbon,
palladium on $Al_2O_3$,
palladium on $CaCO_3$,
palladium on $BaSO_4$,
palladium on $SiO_2$,
iridium on carbon,
iridium on $Al_2O_3$,
iridium on $SiO_2$,
iridium on $CaCO_3$,
iridium on $BaSO_4$,
rhenium on carbon,
rhenium on $Al_2O_3$,
rhenium on $SiO_2$,
rhenium on $CaCO_3$,
rhenium on $BaSO_4$,
rhodium on carbon,
rhodium on $Al_2O_3$,
rhodium on $SiO_2$,
rhodium on $CaCO_3$,
rhodium on $BaSO_4$,
ruthenium on carbon,
ruthenium on $Al_2O_3$,
ruthenium on $CaCO_3$,
ruthenium on $BaSO_4$, and
ruthenium on $SiO_2$.

As stated above, useful catalytic metals include component iridium, palladium, rhodium, nickel, ruthenium, platinum, rhenium; and useful support materials include carbon, alumina, silica, silica-alumina, titania, titania-alumina, titania-silica, barium, calcium, particularly carbon, $SiO_2$, $CaCO_3$, $BaSO_4$ and $Al_2O_3$. A supported catalyst may be made from any combination of the above named metals and support materials. A supported catalyst may also, however, be made from combinations of various metals and/or various support materials selected from subgroup(s) of the foregoing formed by omitting any one or more members from the whole groups as set forth in the lists above. As a result, the supported catalyst may in such instance not only be made from one or more metals and/or support materials selected from subgroup(s) of any size that may be formed from the whole groups as set forth in the lists above, but may also be made in the absence of the members that have been omitted from the whole groups to form the subgroup(s). The subgroup(s) formed by omitting various members from the whole groups in the lists above may, moreover, contain any number of the members of the whole groups such that those members of the whole groups that are excluded to form the subgroup(s) are absent from the subgroup(s). For example, it may be desired in certain instances to run the process in the absence of a catalyst formed from palladium on carbon.

While the weight percent of catalyst on the support is not critical, it will be appreciated that the higher the weight percent of metal, the faster the reaction. A preferred content range of the metal in a supported catalyst is from about 0.1 wt % to about 20 wt % of the whole of the supported catalyst (catalyst weight plus the support weight). A more preferred catalytic metal content range is from about 1 wt % to about 10 wt % by weight of the whole of the supported catalyst. A further preferred catalytic metal content range is from about 3 wt % to about 7 wt % by weight of the whole of the supported catalyst.

Optionally, a metal promoter may be used with the catalytic metal in the method of the present invention. Suitable metal promoters include: 1) those elements from groups 1 and 2 of the periodic table; 2) tin, copper, gold, silver, and combinations thereof; and 3) combinations of group 8 metals of the periodic table in lesser amounts.

Temperature, solvent, catalyst, pressure and mixing rate are all parameters that affect the hydrogenation. The relationships among these parameters may be adjusted to effect the desired conversion, reaction rate, and selectivity in the reaction of the process.

Within the context of the present invention the preferred temperature is from about 25° C. to 250° C., more preferably from about 50° C. to about 150° C., and most preferred from about 50° C. to 100° C. The hydrogen pressure is preferably about 0.1 to about 20 MPa, more preferably about 0.3 to 10 MPa, and most preferably about 0.3 to 4 MPa. The reaction may be performed neat or in the presence of a solvent. Useful solvents include those known in the art of hydrogenation such as hydrocarbons, ethers, and alcohols. Alcohols are most preferred, particularly lower alkanols such as methanol, ethanol, propanol, butanol, and pentanol. Where the reaction is carried out according to the preferred embodiments, selectivites in the range of at least 70% are attainable where selectivites of at least 85% are typical. Selectivity is the weight percent of the converted material that is dihydronepetalactone where the converted material is the portion of the starting material that participates in the hydrogenation reaction.

The process of the present invention may be carried out in batch, sequential batch (i.e. a series of batch reactors) or in continuous mode in any of the equipment customarily employed for continuous processes (see, for example, H. S. Fogler, *Elementary Chemical Reaction Engineering*, Prentice-Hall, Inc., NJ, USA). The condensate water formed as the product of the reaction is removed by separation methods customarily employed for such separations.

Upon completion of the hydrogenation reaction, the resulting mixture of dihydronepetalactone isomer products may be separated by a conventional method, such as for example, by distillation, by crystallization, or by preparative liquid chromatography to yield each highly purified pair of dihydronepetalactone enantiomers. Chiral chromatography may be employed to separate enantiomers.

EXAMPLES

The present invention is further defined in the following examples. These examples, while indicating preferred embodiments of the invention, are given by way of illustration only. From the above discussion and these examples, the artisan can ascertain the essential characteristics of this invention, and, without departing from the spirit and scope thereof, can make various changes and modifications of the invention to adapt it to various usages and conditions.

The following abbreviations are used in the examples:

| | |
|---|---|
| ESCAT | Series of catalysts provided by Engelhard Corp., (E. Windsor, CT). |
| Calsicat Carbon | Catalyst support from Engelhard Corp. |
| Sibunit Carbon | Catalyst support from Inst. of Technical Carbon, (Omsk, Russia). |
| JM-A series | Carbon Catalyst support from Johnson Matthey, Inc., (W. Deptford, NJ). |
| Calgon Carbon | Catalyst support from Calgon Corp. under the brand name of Centaur ® |
| DHNE | Dihydronepetalactone |
| NELA | Nepetalactone |
| GC | Gas chromatography |

Additionally, pressure is referred to in units of psi and MPa, where 14.7 psi is equivalent to 0.101325 MPa (which are both equivalent to 1 atm).

Catalyst Synthesis

A commercially available support such as carbon, alumina, or silica [available from Engelhard Corp. (E. Windsor, Conn.)] was impregnated by incipient wetness with a metal salt. The precursors used were $IrCl_3.3H_2O$, $PdCl_2$ (Alfa Aesar, Wardhill, Mass.), $RhCl_3.xH_2O$ (Alfa Aesar), $RuCl_3.xH_2O$ (Aldrich Chemical Co., Milwaukee, Wis.), $AuCl_3.3H_2O$ (Alfa Aesar), $NiCl_2.6H_2O$ (Alfa Aesar), $H_2PtCl_6$ (Johnson Matthey, Inc., W. Deptford, N.J.), and $Re_2O_7$ (Alfa Aesar).

The samples were dried and reduced at 300–450° C. in $H_2$ for 2 hours.

The carbon used was commercially available as Calsicat Carbon, Sibunit Carbon, or Calgon Carbon. Calsicat Carbon is lot S-96-140 from Engelhard Corp., Beachwood, Ohio. Sibunit Carbon is Sibunit-2 from the Institute of Technical Carbon, 5th Kordnaya, Omsk 64418, Russia. Calgon Carbon is PCB Carbon (commercially available under the registered trademark of Centaur®) from Calgon Corp (Pittsburgh, Pa.).

Experiments 1–46

The present example describes a series of experiments conducted to test the abilities of various catalysts to selectively convert nepetalactone to dihydronepetalactone via hydrogenation. The only variable altered in each experiment was the type of catalyst and support, while the following parameters were held constant (unless specifically noted below):

time—2 hrs;

temperature—50° C.;

$H_2$ pressure—700 psi; and, feedstock—33% nepetalactone in ethanol.

Modifications to these "standard" parameters were made as noted:

Experiments 11, 16, 20, and 22 time—4 hrs; and

Experiment 17 time—3 hrs;

$H_2$ pressure—1000 psi; and feedstock—50% nepetalactone in ethanol.

33% or 50% Nepetalactone in ethanol, and an amount of catalyst and support as indicated in the table below, were added to a 2 ml pressure reactor. The reactor was sealed and charged with 2.75 MPa of $H_2$ and heated to a reaction temperature of 50° C. The pressure was maintained at the desired level during the course of the reaction. The reaction was stopped after a 2 hr period of time and permitted to cool. An internal standard (methoxyethylether) was added into the reaction product mixture.

Analysis of the reaction product mixture was performed by gas chromatography. An HP-6890 GC employed a Chrompack column (CP-WAX 58, 25 M×25 MM) and a flame ionization detector. The temperature program was started at 50° C., then heated at 5° C./min to 80° C., and then heated to 270° C. at a rate of 10° C./min. The column flow rate was 1.5 cc/min He. The injector and detector temperatures were 280° C. and 350° C., respectively. GC analysis permitted determination of dihydronepetalactone selectivity [DHNE Sel (%)], acid selectivity [Acid Sel (%)], and nepetalactone conversion [NELA Con (%)]. DHNE Selectivity is the weight percent of the converted material that is dihydronepetalactone where the converted material is the portion (by weight) of the starting material that participates in the hydrogenation reaction. Acid selectivity is defined as the percent by weight in the converted material of the ring-opened product, methyl-2-isopropyl-5-methylcyclopentanecarboxylate.

For each experiment, the following table (Table 1) lists the catalyst, selectivity of the products, and conversion of the reactant. Data is presented such that the results from each specific catalyst (with variable supports) are presented in series.

TABLE 1

Hydrogenation of Nepetalactone

| Exp't No. | Catalyst | DHNE Sel (%) | Acid Sel (%) | NELA Con (%) |
|---|---|---|---|---|
| 1 | 5% Ir/$Al_2O_3$ | 70.2 | 23.2 | 53.9 |
| 2 | 5% Ir/Calgon C | 72.5 | 21.5 | 34.9 |
| 3 | 5% Ir/Calsicat C | 45.2 | 16.2 | 46.9 |
| 4 | 5% Ir/Sibunit C | 72.8 | 25.3 | 49.3 |
| 5 | 5% Ir/$SiO_2$ | 77.9 | 19.5 | 95.3 |
| 6 | 5% Ni/$Al_2O_3$ | 12.1 | 0.0 | 6.2 |
| 7 | 5% Ni/Calgon C | 8.6 | 0.0 | 7.8 |
| 8 | 5% Ni/Calsicat C | 10.8 | 0.0 | 5.8 |
| 9 | 5% Ni/Sibunit C | 74.6 | 0.0 | 0.7 |
| 10 | 5% Ni/$SiO_2$ | 37.9 | 0.0 | 2.0 |
| 11 | 5% Pd/$Al_2O_3$, JM-A22117-5 | 91.2 | 0.0 | 89.1 |
| 12 | 5% Pd/$Al_2O_3$, JM-A22117-5 | 83.8 | 0.0 | 99.9 |
| 13 | 5% Pd/$Al_2O_3$, JM-A302099-5 | 81.7 | 0.0 | 99.9 |
| 14 | 5% Pd/$Al_2O_3$ | 78.7 | 17.0 | 99.5 |
| 15 | 5% Pd/$BaSO_4$, JM-A22222-5 | 92.1 | 0.0 | 98.8 |
| 16 | 5% Pd/$BaSO_4$, JM-A22222-5 | 70.3 | 0.0 | 68.8 |
| 17 | 5% Pd/C, JM-A503023-5 | 88.8 | 0.0 | 100.0 |
| 18 | 5% Pd/C, JM-A503023-5 | 80.0 | 13.8 | 100.0 |
| 19 | 5% Pd/C, ESCAT-142 | 78.9 | 16.4 | 100.0 |
| 20 | 5% Pd/C, ESCAT-142 | 25.4 | 0.0 | 21.5 |
| 21 | 5% Pd/$CaCO_3$, JM-A21139-5 | 78.3 | 0.0 | 99.8 |
| 22 | 5% Pd/$CaCO_3$, JM-A21139-5 | 71.2 | 0.0 | 65.7 |
| 23 | 5% Pd/Calgon C | 54.3 | 15.9 | 72.6 |
| 24 | 5% Pd/Calsicat C | 73.9 | 13.2 | 94.7 |
| 25 | 5% Pd/Sibunit C | 60.7 | 18.0 | 69.9 |
| 26 | 5% Pd/$SiO_2$ | 72.2 | 16.0 | 100.0 |
| 27 | 5% Pt/$Al_2O_3$ | 13.7 | 54.0 | 100.0 |
| 28 | 5% Pt/Calgon C | 26.1 | 68.0 | 66.9 |
| 29 | 5% Pt/Calsicat C | 15.4 | 54.6 | 79.9 |
| 30 | 5% Pt/Sibunit C | 21.1 | 72.1 | 78.4 |
| 31 | 5% Pt/$SiO_2$ | 13.9 | 46.5 | 91.3 |
| 32 | 5% Re/$Al_2O_3$ | 61.8 | 0.0 | 0.4 |
| 33 | 5% Re/Calgon C | 12.8 | 0.0 | 1.8 |
| 34 | 5% Re/Calsicat C | 15.5 | 3.9 | 33.6 |
| 35 | 5% Re/Sibunit C | 19.1 | 5.0 | 22.3 |
| 36 | 5% Re/$SiO_2$ | 24.3 | 6.2 | 24.9 |
| 37 | 5% Rh/$Al_2O_3$ | 82.2 | 15.6 | 99.9 |
| 38 | 5% Rh/Calgon C | 80.3 | 12.1 | 99.1 |
| 39 | 5% Rh/Calsicat C | 68.6 | 12.2 | 98.4 |
| 40 | 5% Rh/Sibunit C | 81.2 | 15.9 | 99.0 |
| 41 | 5% Rh/$SiO_2$ | 83.4 | 14.5 | 99.9 |
| 42 | 5% Ru/$Al_2O_3$ | 67.0 | 11.2 | 91.5 |
| 43 | 5% Ru/Calgon C | 36.6 | 7.6 | 73.1 |
| 44 | 5% Ru/Calsicat C | 41.0 | 6.8 | 69.6 |
| 45 | 5% Ru/Sibunit C | 71.5 | 15.5 | 75.1 |
| 46 | 5% Ru/$SiO_2$ | 82.3 | 13.0 | 97.8 |

Preferred combinations of catalytic metal and support system includes

Ir/C (Sibunit C, Calsicat C, and Calgon C),

Ir/$Al_2O_3$,

Ir/$SiO_2$,

Pd/C (Sibunit C, Calsicat C, Calgon C, JM-A series, and ESCAT-142),

Pd/$Al_2O_3$,

Pd/$BaSO_4$,

Pd/$CaCO_3$,

Pd/$SiO_2$,

Rh/C (Sibunit C, Calsicat C, and Calgon C),

Rh/$Al_2O_3$,

Rh/$SiO_2$,

Ru/C (Sibunit C, Calsicat C, and Calgon C),

Ru/$Al_2O_3$, and

Ru/$SiO_2$.

For the majority of experiments with these preferred combinations of catalytic metal and support system, yields of dihydronepetalactone were at least 70% selectivity. Experiment 15 achieved the highest yield of dihydronepetalactone (92.1%) with 98.8% conversion of nepetalactone using Pd/$BaSO_4$.

Thus, a variety of Group 8 metals on various supports have been demonstrated to be active for hydrogenation of nepetalactone, permitting high yields in 2–4 hrs. This will result in significantly reduced scale-up costs as compared to methods of hydrogenation previously reported in the literature for production of dihydronepetalactones.

What is claimed is:

1. A process for the production of a dihydronepetalactone of formula (II) comprising hydrogenating a nepetalactone of formula (I) according to the following scheme:

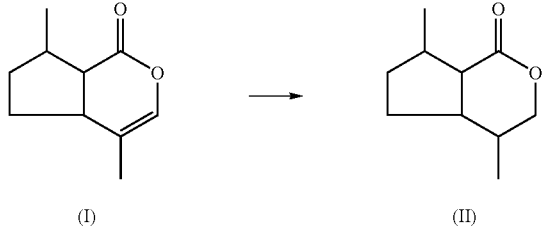

(I)  (II)

in the presence of a catalytic metal that is not nickel, platinum or palladium.

2. The process as recited in claim 1 wherein the catalytic metal is selected from the group consisting of ruthenium, rhenium, rhodium, iridium, compounds thereof, and combinations thereof.

3. The process as recited in claim 1 wherein the catalytic metal is supported on a catalyst support.

4. The process as recited in claim 3 wherein the catalyst support is selected from the group consisting of carbon, alumina, silica, silica-alumina, titania, titania-alumina, titania-silica, barium, calcium, compounds thereof, and combinations thereof.

5. The process as recited in claim 3 wherein the catalytic metal content is from about 0.1% to about 20%.

6. The process as recited in claim 1 which is effected in the presence of a metal promoter.

7. The process as recited in claim 6 wherein the metal promoter is selected from the group consisting of tin, copper, gold, silver, and combinations thereof.

8. The process as recited in claim 1 which is performed at a temperature of about 25° C. to about 250° C. and a pressure of about 0.1 MPa to about 20 MPa.

9. The process as recited in claim 1 which yields dihydronepetalactone with at least 70% selectivity.

10. The process as recited in claim 3 wherein the catalytic metal is selected from the group consisting of Ir and Rh; wherein the support is selected from the group consisting of C, $SiO_2$, $CaCO_3$, $BaSO_4$ and $Al_2O_3$; and wherein the process is performed at a temperature of about 50° C. to about 150° C., and a pressure of about 0.3 MPa to about 4 MPa.

11. The process as recited in claim 3 wherein the catalytic metal and support is selected from the group consisting of
iridium on carbon,
iridium on $Al_2O_3$,
iridium on $SiO_2$,
iridium on $CaCO_3$,
iridium on $BaSO_4$,
rhenium on carbon,
rhenium on $Al_2O_3$,
rhenium on $SiO_2$,
rhenium on $CaCO_3$,
rhenium on $BaSO_4$,
rhodium on carbon,
rhodium on $Al_2O_3$,
rhodium on $SiO_2$,
rhodium on $CaCO_3$,
rhodium on $BaSO_4$,
ruthenium on carbon,
ruthenium on $Al_2O_3$,
ruthenium on $CaCO_3$,
ruthenium on $BaSO_4$,
ruthenium on $SiO_2$ and
combinations thereof.

12. A process for the production of a dihydronepetalactone of formula (II) comprising hydrogenating a nepetalactone of formula (I) according to the following scheme:

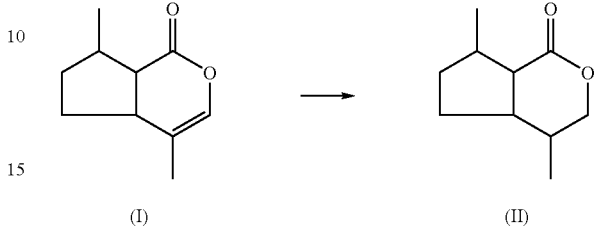

(I)  (II)

in the presence of a catalytic metal selected from one or more members of the group consisting of nickel supported on a catalyst support, elemental platinum, platinum supported on a catalyst support, palladium not supported on a catalyst support, and palladium supported on a catalyst support that is not $SrCO_3$.

13. The process as recited in claim 12 wherein, in a supported species, the catalyst support is selected from the group consisting of carbon, alumina, silica, silica-alumina, titania, titania-alumina, titania-silica, barium, calcium, compounds thereof, and combinations thereof.

14. The process as recited in claim 12 wherein, in a supported species, the catalytic metal content is from about 0.1% to about 20%.

15. The process as recited in claim 12 which is effected in the presence of a metal promoter.

16. The process as recited in claim 15 wherein the metal promoter is selected from the group consisting of tin, copper, gold, silver, and combinations thereof.

17. The process as recited in claim 12 which is performed at a temperature of about 25° C. to about 250° C. and a pressure of about 0.1 MPa to about 20 MPa.

18. The process as recited in claim 1 which yields dihydronepetalactone with at least 70% selectivity.

19. The process as recited in claim 12 wherein, in a supported species, the support is selected from the group consisting of C, $SiO_2$, $CaCO_3$, $BaSO_4$ and $Al_2O_3$; and wherein the process is performed at a temperature of about 50° C. to about 150° C., and a pressure of about 0.3 MPa to about 4 MPa.

20. The process as recited in claim 12 wherein, in a supported species, the catalytic metal and support are selected from the group consisting of
nickel on carbon,
nickel on $Al_2O_3$,
nickel on $CaCO_3$,
nickel on $BaSO_4$,
nickel on $SiO_2$,
platinum on carbon,
platinum on $Al_2O_3$,
platinum on $CaCO_3$,
platinum on $BaSO_4$,
platinum on $SiO_2$,
palladium on carbon,
palladium on $Al_2O_3$,
palladium on $CaCO_3$,
palladium on $BaSO_4$,
palladium on $SiO_2$, and
combinations thereof.

* * * * *